United States Patent [19]

Kuhne

[11] Patent Number: 4,725,437

[45] Date of Patent: Feb. 16, 1988

[54] AQUEOUS CHLORITE MATRIX SOLUTION

[75] Inventor: Friedrich W. Kuhne, Heidelberg, Fed. Rep. of Germany

[73] Assignee: OXO Chemie GmbH, Fed. Rep. of Germany

[21] Appl. No.: 857,953

[22] Filed: May 1, 1986

[30] Foreign Application Priority Data

May 2, 1985 [DE] Fed. Rep. of Germany ....... 3515745

[51] Int. Cl.$^4$ ............................................. A61K 33/40
[52] U.S. Cl. .................................... 424/130; 424/149
[58] Field of Search ................................ 424/149, 130

[56] References Cited

U.S. PATENT DOCUMENTS 4,035,483 7/1977 Bunyan ............................... 424/149
4,507,285 3/1985 Kühne ................................. 426/130

OTHER PUBLICATIONS

Oxyferin ®, Jan. 1987, Brochure of OXO Chemie GmbH.

Youngman et al., Free Rad. Res. Comm., vol. 1, No. 5, pp. 311–319.
Stahl et al., Brit. J. of Derm., 1986, 115 Supplement 31, 142–147.
Hinz et al., Lancet, Apr. 12, 1986, pp. 825–828, Sep. 15, 1984, p. 630.
Gillissen et al., Arzneimittel-Forschung, International Symposium Cancer: Prospective for Control, Beijing, China, Aug. 18–21, 1985.
"Reaktive Sauerstoffspezies in der Medizin", pub. Springer-Verlag, 1986.
Chemical Abstracts 99:218607u, 1983 (Kuehne).

*Primary Examiner*—Leonard Schenkman
*Attorney, Agent, or Firm*—Franklin D. Wolffe; Morris Fidelman

[57] ABSTRACT

An aqueous solution of a chemically stabilized chlorite matrix for intravenous and perioperative administration in a dosed amount of $6.2 \times 10^{-6}$ mole of $ClO_2-$ to $9.3 \times 10^{-5}$ mole of $ClO_2-$ per kg of body weight to humans and animals is described.

2 Claims, 1 Drawing Figure

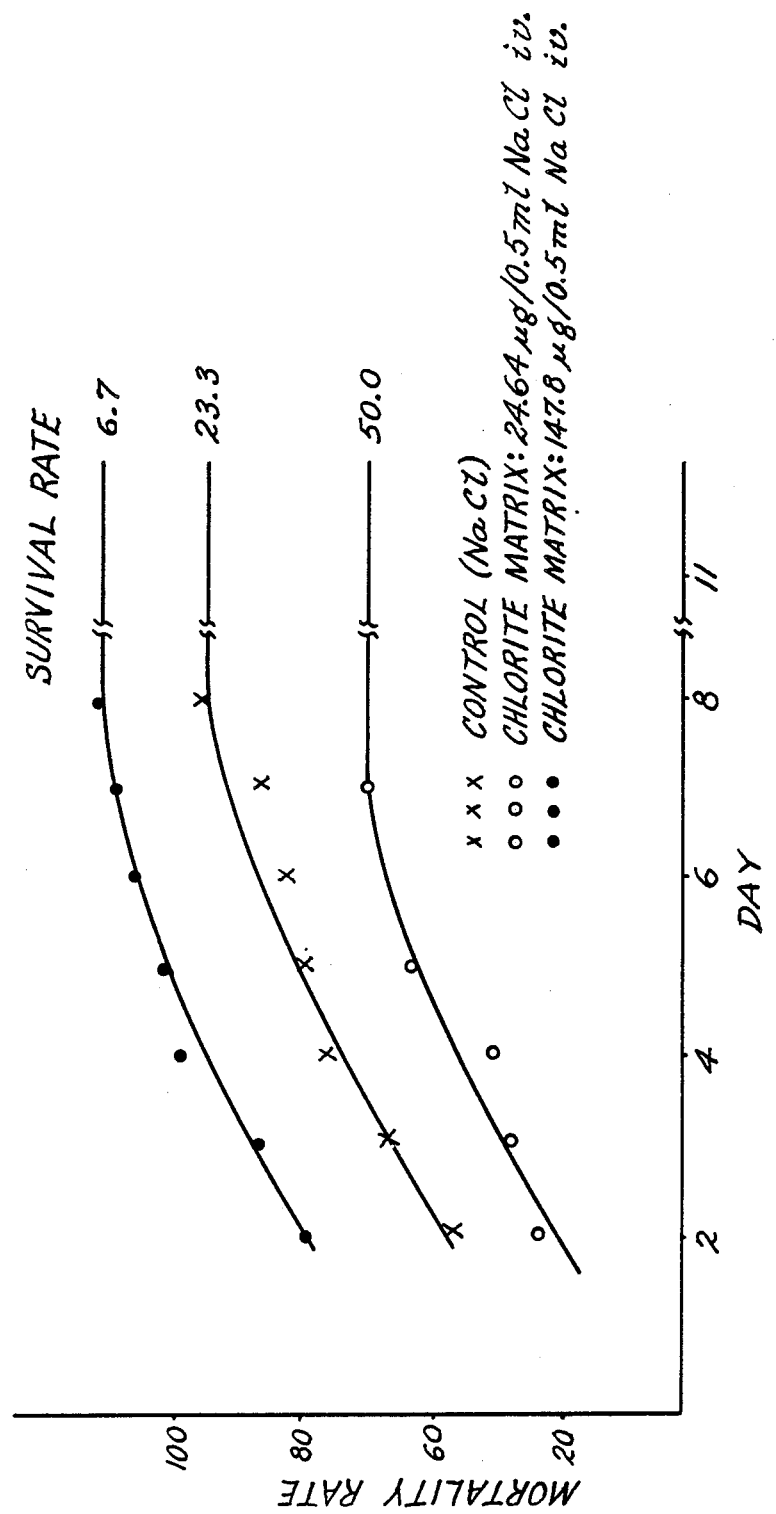

AQUEOUS CHLORITE MATRIX SOLUTION

The invention relates to an aqueous solution of a chemically stabilized chlorite matrix for intravenous and perioperative administration.

Stabilized chlorite matrices containing activated oxygen are disclosed in German Offenlegungsschrift No. 3,213,389 for which the corresponding U.S. Pat. is No. 4,507,285, and they are already being used successfully as wound-treatment agents in the form of aqueous solutions (In the literature concurrent herewith, TCDO, an acronym for Tetrachloradecaoxygen, has been emloyed in identification of the matrix of this invention).

Attempts to administer, intravenously, or by continuous drip, to infected experimental animals those chlorite matrix solutions which are used for wound treatments have failed because the effects observed were by no means therapeutic but, on the contrary, toxic. The use of these solutions by this route appeared to be ruled out.

It has now been found, very surprisingly, that, in contrast to the prevailing opinion, it is possible to administer, also intravenously and perioperatively, solutions of a stabilized chlorite matrix in a very particular concentration range per kg of body weight of the treated human or animal since, at the particular dosage, the effect which occurs is not toxic but effectively therapeutic.

An aqueous solution of a chemically stabilized chlorite matrix is suitable for intravenous and perioperative administration in a dosed amount of $6.2 \times 10^{-6}$ mole of $ClO_2-$ to $9.3 \times 10^{-5}$ mole of $ClO_2-$ per kg of body weight in humans and animals.

The solution contains the chlorite matrix in a concentration of 12 to 72 $\mu$mol of $ClO_2-$ per ml.

The positive action of a solution of this type was demonstrated in infected experimental animals. Experiments were carried out with therapeutic amounts of 0.60 to 60 $\mu$mol of $ClO_2-$ per kg of body weight, which were administered in the form of a solution ready for use. Experimental results:

Use was made of an aqueous isotonic solution of a matrix of chlorite ions with stabilized activated oxygen entrapped therein. The test substance contained a concentration of 60 $\mu$mol/l based on chlorite.

The dose was adjusted using sterile phys. NaCl solution.

Experimental animals

Male Balb/cABOM mice (Bomholtgord, Ry, Denmark) of body weight 20±1 g.

n=30 animals per group.

The experimental infection was effected with Candida albicans ATCC 10231. The microorganisms were cultured in liquid medium, taken from the log phase of growth, washed, counted under the microscope and taken up in sterile phys. NaCl solution to a density of $6 \times 10^6$ cells/0.25 ml, corresponding to the ID 75 determined in preliminary experiments. The experimental infection was effected by i.v. injection of this dose.

The animals were treated by a single i.v. injection of the test solution 1 h after the infection. 2 groups were set up with different doses of the test substance for this purpose (phys. NaCl solution for the controls).

Each animal in one group received 24.64 $\mu$g, and each in another group received 147.8 $\mu$g, of the test substance in 0.5 ml, corresponding to 0.20 ml of the initial solution per kg=1.232 mg/kg and to 1.20 ml of the test substance per kg=7.392 mg/kg, respectively.

Preliminary experiments had shown that a single injection of these doses into the tail veins of the animals did not cause any necroses.

The infection experiments showed that a single administration of the smaller dose results in an unambiguous improvement in the chances of survival with this experimental infection, but that a single administration of the higher dose just as unambiguously results in a deterioration. This is evident both from the changes in the mortality rate and from the number of surviving animals in the three groups.

The results are illustrated in the graph which is attached and which shows the mortality rate and survival rate after 11 days. The untreated experimental animals (control experiments) showed a survival rate of 23.3%, those experimental animals treated with a 0.2 $\mu$g/0.5 ml chlorite matrix solution showed a survival rate of 50%, whereas the 1.2 $\mu$g/0.5 ml chlorite matrix solution proved to be extremely toxic, with a survival rate of 6.7%. The positive effect of a 0.2 $\mu$g/0.5 ml solution is unexpectedly high, whereas a 1.2 $\mu$g/0.5 ml solution clearly confirms the current opinion of those skilled in the art.

Furthermore, experiments which are in progress show that chlorite matrix solutions stabilized otherwise than with oxygen can also be used. The chlorite matrix ions are proving to be suitable for appropriate intravenous and perioperative use even in a form stabilized otherwise than with oxygen.

I claim:

1. A method for treating infection in humans and animals which comprises administering to said human or animal intravenously
   an aqueous solution of a stabilized activated oxygen-containing chlorite matrix
   in a dosed amount of from $6.2 \times 10^{-6}$ mole to $9.3 \times 10^{-5}$ mole of said matrix per kg of body weight of said human or animal.

2. A method as defined by claim 1 wherein said matrix is present in said aqueous solution in a concentration of from 12 to 72 $\mu$mol of said matrix per ml.

* * * * *